United States Patent [19]

Kurtzer

[11] Patent Number: 5,168,863
[45] Date of Patent: Dec. 8, 1992

[54] STERILE ENDOSCOPIC SYSTEM

[75] Inventor: Stephen M. Kurtzer, Santa Barbara, Calif.

[73] Assignee: Medical Concepts, Inc., Goleta, Calif.

[21] Appl. No.: 572,705

[22] Filed: Aug. 27, 1990

[51] Int. Cl.⁵ .............................................. A61B 1/00
[52] U.S. Cl. .................................... 128/4; 604/17; 604/263; 206/363
[58] Field of Search ............ 128/4, 6, 846, 849, 128/856; 604/163, 171, 172, 263; 206/69, 363, 364, 438

[56] References Cited

U.S. PATENT DOCUMENTS

| | | | |
|---|---|---|---|
| 4,515,592 | 5/1985 | Frankhouser | 604/171 |
| 4,522,196 | 6/1985 | Cunningham et al. | 128/4 |
| 4,593,699 | 6/1986 | Poncy et al. | 128/662.03 |
| 4,646,722 | 3/1987 | Silverstein et al. | 128/4 |
| 4,721,097 | 1/1988 | D'Amelio | 128/4 |
| 4,817,592 | 4/1989 | Auchinleck et al. | 206/438 |
| 4,825,850 | 5/1989 | Opie et al. | 128/4 |
| 4,834,710 | 5/1989 | Fleck | 604/163 |
| 5,010,876 | 4/1991 | Henley et al. | 206/438 |

FOREIGN PATENT DOCUMENTS 8900832 2/1989 PCT Int'l Appl. .................. 128/4

Primary Examiner—Stephen C. Pellegrino
Assistant Examiner—Ralph A. Lewis
Attorney, Agent, or Firm—Elliott N. Kramsky

[57] ABSTRACT

Apparatus for providing a sterile operating environment for endoscopic diagnosis and/or surgery. A covering comprises a pair of generally orthogonally arranged component bags. Each of the component bags is of an accordian-like extendible type. The component bags are joined adjacent the open end of one bag and an aperture adjacent the open end of the other bag. The open end of the second bag is engaged either to a sterile endoscopic probe preferably of the disposable type or to a shield for enclosing the distal end of an endoscope. The entire apparatus is sterilized and configured so that the component bags can be extended along the camera and light guide cables of the endoscopic system so that resistant spores, bacteria and viruses cannot contaminate the open incision.

18 Claims, 3 Drawing Sheets

STERILE ENDOSCOPIC SYSTEM

BACKGROUND

1. Field of the Invention

The present invention relates to endoscopic systems. More particularly, this invention pertains to apparatus for maintaining a sterile environment while performing diagnosis and/or surgery by means of an otherwise-conventional endoscopic system of the type that includes an endoscope, a fiber-optic light guide cable and a camera.

2. Description of the Prior Art

The uses of endoscopy have expanded greatly over the past few years. Endoscopic procedures minimize the trauma to the patient and accordingly lessen the amount of patient time required, both in and out of the hospital. Recently, endoscopy has gained widespread acceptance throughout so-called "general" surgery. For example, laparoscopic cholecystectomies (removal of the gall bladder) are now common procedures.

In performing endoscopic general surgery, a camera head must be employed to process the images of internal organs that are transmitted through the optical system of the endoscope. Such a camera permits all members of the surgical team to view the same anatomical site simultaneously. By producing the image on a video screen, the auxiliary video mechanisms of endoscopy effectively replace the much larger incisions of conventional surgery with relatively insignificant punctures.

The complete endoscopic system, which generally includes an endoscope, an optical adapter, a camera head with attached cable and a fiber optic light guide cable for transmitting optical energy from a light source and an electrical cable for communicating with the camera's electronics, is maintained in close proximity to the patient throughout endoscopic procedures. Such components comprise an amalgam of stainless steel, brass, glass, solder, electronic components and rubber parts. The differing natures of these compositions ultimately limit the safety of endoscopic procedures as the instruments themselves can contribute to the risk of infection.

Generally, surgical instruments are sterilized between cases by means of an autoclave that subjects them to sufficiently extreme pressures and temperatures to prevent the survival of biological organisms. Unfortunately, the combination of disparate materials employed within a conventional endoscopic system does not permit autoclaving between surgical cases due to the widely varying rates of thermally-induced expansion and contraction. Such differences can stress electronic components, seals and glass to the breaking point. Other methods, such as exposure to ethylene oxide (gas) or gamma radiation require long sterilization cycles that are inappropriate for inter-case use.

As a result, endoscopes are disinfected, but not sterilized between procedures. Generally disinfection is more than sufficient to protect the patient and the doctor from infection, killing most surface bacteria, viruses and spores. However, some resistant bacteria, viruses and pathogenic spores can remain. There exists evidence, for example, that disinfection may not significantly kill hepatitis B and HIV viruses and is therefore not sufficient in today's world of resistant bacteria and viruses.

SUMMARY OF THE INVENTION

The present invention addresses the foregoing and additional shortcomings of the prior art by providing, in a first aspect, apparatus for use with an endoscopic system of the type that includes a light guide cable for transmitting light to the system, a camera head for processing an image of internal structures and a camera cable for transmitting power and data between the camera head and an electronic processor. Such apparatus includes an endoscope. A first elongated open bag has a transversely-oriented aperture adjacent the proximal end of the endoscope. A second elongated open bag is provided. One end of the second bag is sealably secured to the first bag so that the interior of the first bag communicates with the interior of the second bag through the aperture so that the first bag accommodates the camera head and camera cable. Means, fixed to the end of the first bag, are provided for attaching such bag to the endoscope in the region of attachment of the light guide cable to the endoscope. The exposed outer surfaces of the endoscope and the first and second bags are sterile.

In another aspect, the invention provides apparatus for use with an endoscopic system of the type that includes an endoscope, an optical adapter attached between the proximal end of the endoscope and a camera head, a light guide cable, and a camera cable for transmitting power and data between the camera head and a source. A first elongated open component bag has a transversely-oriented aperture adjacent an end. A second elongated open bag, one end of which is sealably secured to the first bag so that the interior of the first bag communicates with the interior of the second bag through such aperture, is also provided. An elongated cylindrical shield is of a length and an inner diameter that exceed the length and outer diameter of the endoscopic probe. Means are provided for attaching the proximal end of the shield to the end of the first bag. The outer surfaces of the shield and the first and second component bags are sterile.

The foregoing and additional features of the invention will become apparent from the detailed description that follows. Such description is accompanied by a set of drawing figures. Numerals of the written description, corresponding to those of the drawing figures, point to the various features of the invention. Like numerals refer to like features throughout both the written description and the drawing figures.

DETAILED DESCRIPTION

Figure 1A:
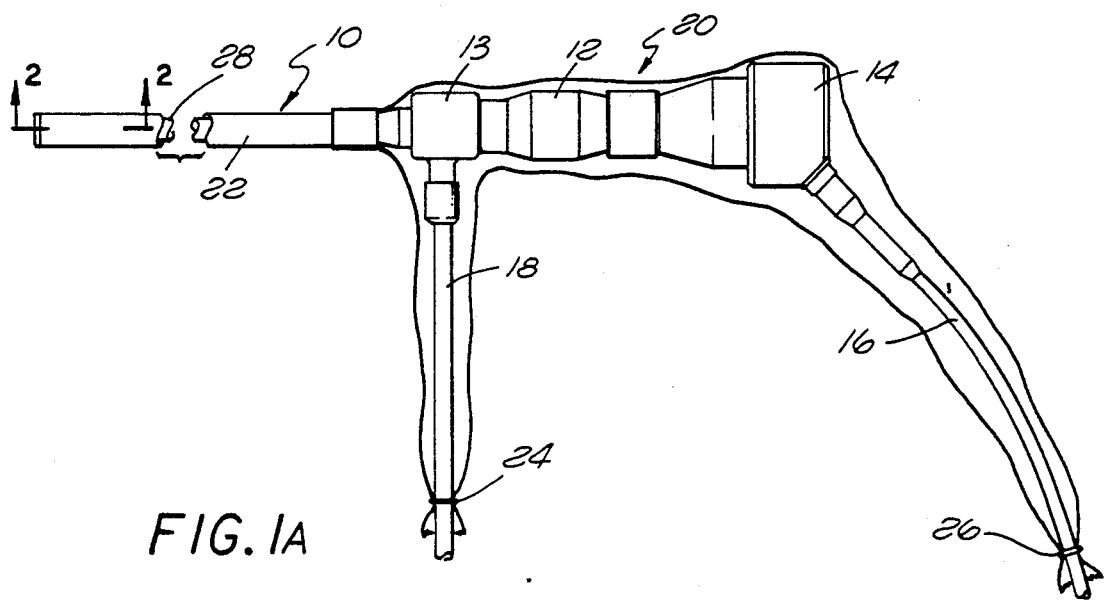
FIGS. 1A and 1B illustrate the apparatus of the invention engaged to otherwise-conventional endoscopic systems, that of FIG. 1A being an endoscopic system wherein the eyepiece has been removed for utilization of a particular type of optical adapter while that of FIG. 1B discloses a system that includes an endoscope eyepiece.
Figure 1B:
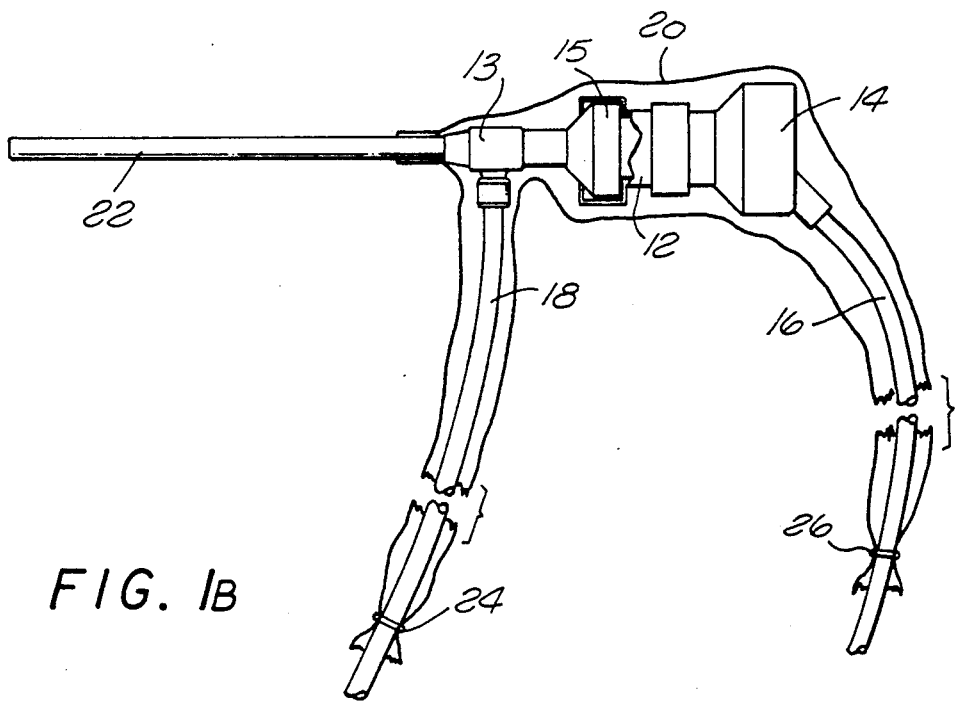

FIGS. 1A and 1B illustrate the apparatus of the invention engaged to otherwise conventional endoscopic systems. The system of FIG. 1A corresponds to a system that employs a particular type of optical adapter that requires removal of an endoscope eyepiece such as that disclosed, for example, in U.S. Pat. No. 4,807,594 of Chatenever entitled "Adapter Assembly For Endoscope Camera". That existing endoscopic system includes an elongated probe 10 that is joined to a hub 13 which together forms the distal end of the endoscope. An adapter 12 includes a number of mechanical and optical components that attach to the proximal end of the endoscope for transmitting the image of the internal organs relayed from the distal (probe 10) to the proximal end of the endoscope for subsequent receipt and conversion to video electronic signals at a camera head 14. The particular type of endoscopic system shown in FIG. 1A differs most significantly from that of FIG. 1B in that the endoscopic eyepiece has been removed and replaced with an ocular adapter that functions to overcome the fogging effect that can result, in part, from the existence of a temperature gradient between the endoscope and the optical adapter 12. In the endoscopic system of FIG. 1B, an eyepiece 15 is located at the proximal end of the endoscope (a side of the optical adapter 12 has been removed to facilitate observation.) Otherwise, the endoscopic systems of FIGS. 1A and 1B are sufficiently similar that the following description will apply to either one.

A cable 16 provides electrical communication between the camera head 14 and a power source (not shown) and processing and display circuitry (not shown). Such circuitry receives, processes and displays a video image for observation by the operating physician and assistants. Similarly, another (light guide) cable 18, in communication with a light source (not shown), transmits light for illuminating the body cavity to the endoscopic system through a hub 13. Such light is subsequently transmitted through the optical fibers within the elongated probe to illuminate tissue adjacent the distal end thereof. The image of such tissue is transmitted through an optical system for subsequent video and electronic processing by the adapter 12, the camera head 14 and, ultimately, a distant video display (not shown).

As discussed above, it is not possible to sterilize all essential components of existing endoscopic systems by autoclave for daily re-use in the operating environment as a consequence of the requisite material compositions of such essential elements as the probe 10 and the camera head 14. The present invention therefore provides apparatus for overcoming this extremely significant shortcoming of existing endoscopic systems by providing an easy-to-install, economical apparatus that does not interfere with the operation of such a system while effectively eliminating the endoscopic system as a source of potential contamination. Such apparatus includes a soft, flexible generally Y-shaped covering 20 that is joined to an elongated probe shield 22. The apparatus is easily installed by the physician and/or operating assistant in the operating room environment.

The entire apparatus is initially sterilized by a conventional method such as exposure to ethylene oxide or gamma radiation and is of sufficiently economical design and manufacture to permit single procedure use. Furthermore, the invention is not so dissimilar from other recognized operating room paraphernalia, such as the so-called "turkey bag", to require significant training and/or familiarization for proper installation by operating room personnel.

The covering 20 is preferably formed of a substantially impermeable plastic that may be formed in very soft, thin sheets such as commercially available polyethylene. Such material can provide an effective barrier for containing resistant bacteria, spores and viruses at a thickness of one (1) or two (2) mils. The rigid shield 22 that acts as a sheath for the probe may be formed of a plastic composition (such as that which is commercially available under the "DELRIN" trademark) of one (1) to two (2) millimeter wall thickness. Alternatively, the shield 22 may be formed of a relatively-inexpensive metal or steel of like thickness. A conventional endoscope for abdominal surgery may have a diameter of 5 to 10 millimeters. Thus the shield 22 does not add noticeably to the thickness of the probe 10.

It is essential that a sterile environment be maintained so that the resistant spores, bacteria and viruses that remain after disinfection do not contaminate the patient's open wound. Furthermore, neither the light cable 18 nor the camera cable 16 is sterile. The inventor has taken advantage of the fact that spores, viruses and bacteria cannot migrate sua sponte. Accordingly, he has found that an adequate sterile environment may be provided if the exposed surfaces of the elongated cables are restricted to areas sufficiently distant from the gloves or other areas of the physician that might contact the open wound to prevent such transportation of contaminants. Fastening means (which need not be sterile) such as plastic tie wraps 24 and 26 (or, for that matter, rubber bands) may be used to secure the ends of the two bag-like segments of the covering 20 about the cables 18 and 16, at safe distances from the patient. Generally, a light guide cable 18 is approximately six (6) feet in length while a camera cable 16 is from 10 to 15 feet long. Good practice suggests that the entire length of the light guide cable 18 should be covered while a minimum of a nine (9) feet of the camera cable 16 should be encompassed by the sterile covering 20. In this way, the physician can be reasonably assured that no portion of the endoscopic system will serve as a source of spore, viral or bacterial contamination of the surgical incision.

Figure 2:
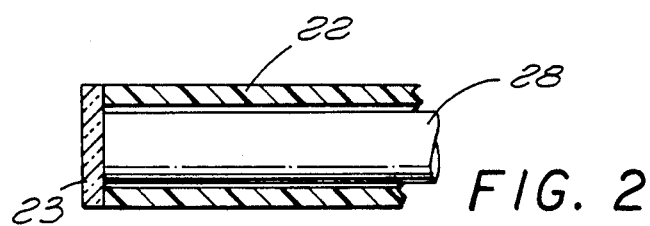
FIG. 2 is a detailed cross sectional view of the distal end of the endoscope shield taken at line 2—2 of FIG. 1A.

FIG. 2 is a detailed cross sectional view of the distal end of the endoscope shield 22 taken at line 2—2 of FIG. 1. As can be seen, the non-sterile endoscope probe 28 fits within the sterilized shield 22, the shield's length and diameter slightly exceeding that of the probe 28. A window 23 of optical quality glass or plastic is fixed to the end of the shield 22. The window 23 is optically clear and may or may not include a special coating. A silicone type plastic glue may be employed to secure the window 23 to the shield 22.

Figure 3:
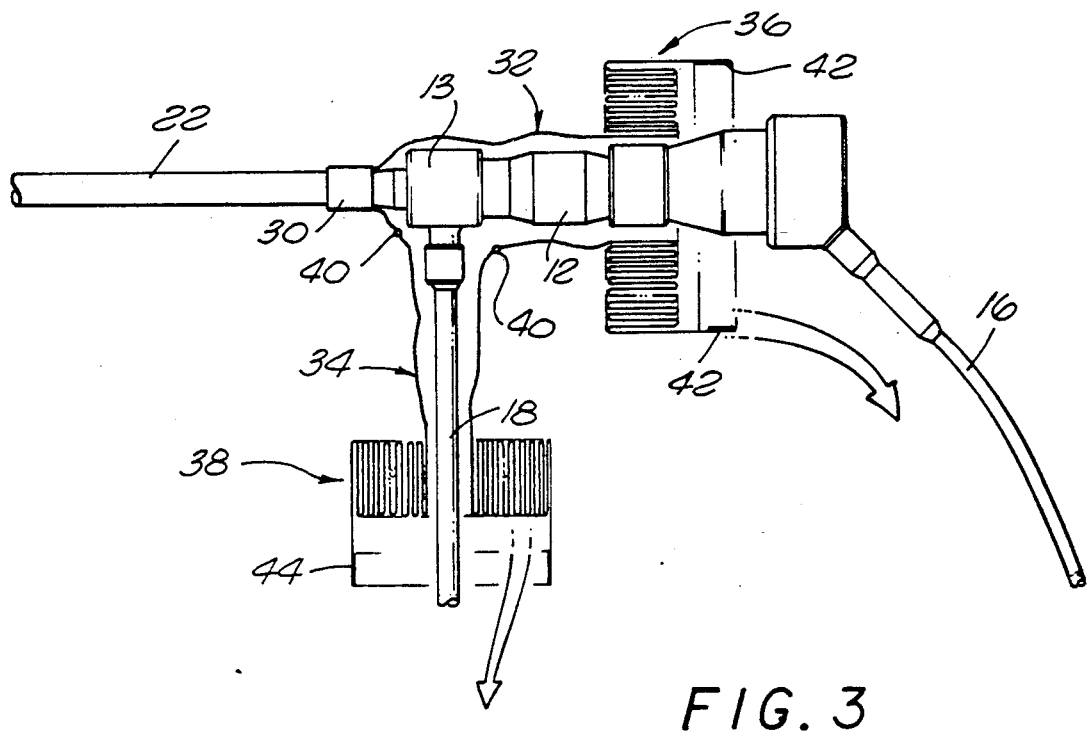
FIG. 3 is a detailed plan view of apparatus in accordance with the invention taken during the process of affixation to a conventional endoscopic system.

FIG. 3 is a detailed plan view of the invention during assembly or affixation to the conventional endoscopic system described above. As explained above, the hub 13 communicates with the endoscope probe 28, the light guide cable 18 and the adapter 12. Accordingly, the covering 20 (in combination with the shield 22) must present an easily installable apparatus, free from contamination during installation and yet capable of completely shielding the irregular endoscopic system's geometry from the operating area.

Means 30 are provided for adhering the sterile covering 20 to the sterile shield 22. Such means 30 may comprise a water tight adhesive wrap (non-water soluble adhesive). The covering 20 comprises a composite of two substantially-orthogonally arranged, expandable accordian-like component bags 32 and 34 of polyethylene or like material. Each of the individual components 32 and 34 resembles the basic turkey bag employed in many medical settings. The component bags 32 and 34 are shown incompletely extended, leaving non-extended multiple folded layer groupings 36 and 38 respectively. Pairs of tabs 42 and 44 are located at the ends of the component bags 32 and 34 to facilitate extension of the folded layer groupings 36 and 38 (in directions indicated in the figure by arrows) to cover the non-sterile cables 16 and 18. The component bags 32 and 34 are mutually sealably secured at a heat sealed seam 40.

Figure 4:
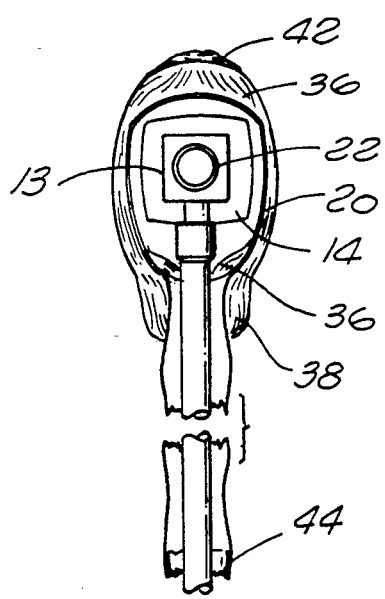
FIG. 4 is a partial front view of the invention affixed to a conventional endoscopic system.

FIG. 4 is a front view of the apparatus of the invention. As can be seen, covering 20 fits somewhat loosely over the endoscopic system. Accordingly, the disposable sterile apparatus can be employed with endoscopic systems of varying dimension without substantial modification. It is only essential that the invention be of sufficient size to effectively sterilize the environment close to the patient (thereby preventing the endoscopic system from serving as a source of infection and contamination) while adding only a limited amount of material so that the handling of the instrument is not made overly complex.

Figure 5:
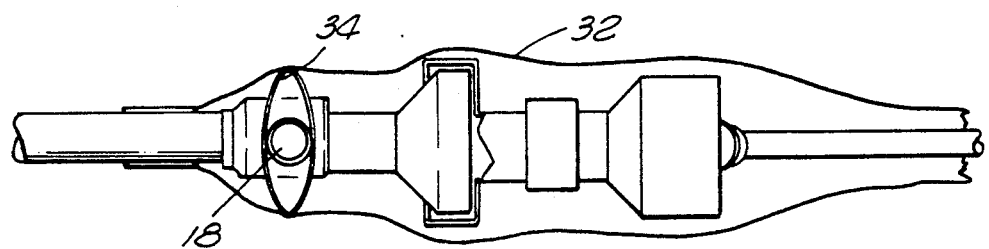
FIG. 5 is a partial bottom plan view of the invention engaged to a conventional endoscopic system.

FIG. 5 is a bottom plan view of the invention engaged to an endoscopic system. As is seen, the heat sealed seam 40 that secures the component bag 34 to the component bag 32 is essentially of elliptical shape, leaving an opening at its interior for the cable 18 to pass to the light source (not shown).

Figure 6:
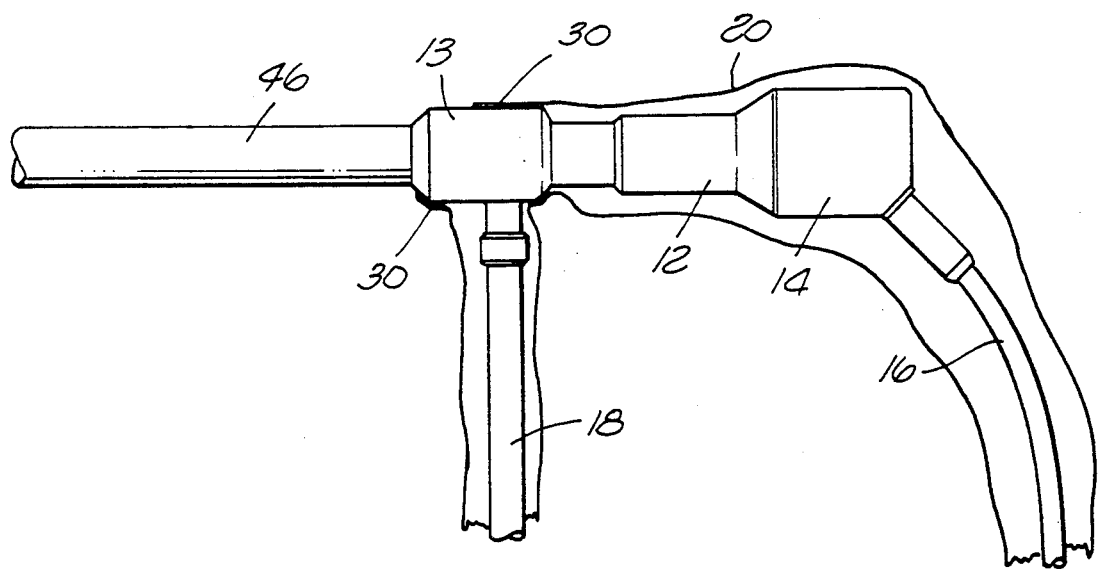
FIG. 6 illustrates an alternative embodiment of the invention.

FIG. 6 is an illustration of an alternative embodiment of the apparatus of the invention engaged to an otherwise-conventional endoscopic system. The apparatus of FIG. 6 is generally arranged like that of the prior embodiment (FIGS. 1 through 5) as indicated by the like numerals. However, an endoscope 46 (including both a probe element and a hub 13) is substituted for the probe shield 22 of the prior described embodiment. Such an endoscope 46 might comprise a lower quality, lower cost instrument that has been pre-sterilized along with the covering 20 for economical single-procedure usage. A so-called "disposable" endoscope can be of adequate optical quality for use in standard endoscopic procedures.

Unlike the prior embodiment, the hub 13 preferably comprises a portion of the sterile unit of FIG. 6 as packaged for sale and use. The covering 20 is directly affixed by means 30 to the sterilized endoscope 46 and is packaged with the covering 20 affixed thereto. The physician or assistant adapts this apparatus to an endoscopic system by engaging the hub 13 to the endoscopic adapter 12 while maintaining his gloved hands upon the exterior of the covering 20 to avoid contamination. Once the disposable endoscope 46 has been properly engaged to the adapter, the physician pulls on the tabs 42 to extend the accordian-like component bag 32 an appropriate distance past the camera head 14 (which, in the illustrated arrangement, is of a type that is integral with the adapter 12) and then secures it to the camera cable 16. When the bag 32 is extended, the seam 40 is caused to surround the light guide post of the hub 13. The physician or assistant can now attach the light guide cable 18 to the post and, by pulling the tabs 44, extend the component bag 34 a satisfactory distance from the operating area before securing the end of the bag 34 to the cable 18.

In contrast, when employing the prior described embodiment, the physician first inserts the elongated (non-sterile) endoscope 28 into the shield 22 after dropping the instrument into the component bag 32 (partly extended from its fully folded shape). All the while, of course, the physician holds the instrument by the outside of the covering 20 to avoid contamination of his gloved hands.

Once the endoscope 28 has been fitted into the shield 22, the component bag 32 is extended by pulling the pair of tabs 42 and is then tied to the cable 16. As before, even partial extension of the component bag 32 will position the light guide post of the hub 13 within the seam 40. Thus an opening is made through the folded component bag 34 for attaching the light guide cable 18. After attachment, the bag 34 is extended by pulling the tabs 44 and tied (at an appropriate distance) to the cable 18.

Thus it is seen that the present invention provides novel apparatus for sterilizing the working environment during an endoscopic procedure. By applying the teachings of this invention, one may be assured that the beneficial endoscopic system does not itself serve as a source of contamination and/or infection. Accordingly, the benefits of such relatively non-invasive procedures are not compromised by an increased risk of infection.

While this invention has been described with reference to its presently preferred embodiment, it is not limited thereto. Rather, this invention is limited only insofar as defined by the following set of claims and includes all equivalents thereof.

What is claimed is:

1. Apparatus for use with an endoscopic system that includes a sterilized rigid endoscope, a light guide cable for transmitting light to said endoscope, a camera head for processing an image of internal structures and a camera cable for transmitting power and data between said camera head and an electronic processor, said apparatus comprising, in combination:

a) a first elongated component bag having opposed, open ends and having a transversely-oriented aperture adjacent a first open end;
   b) a second elongated component bag having opposed, open ends, a first end of said second bag being sealably engaged to said first bag at said transverse aperture whereby the interior of said first bag communicates with the interior of said second bag through said aperture so that said first bag can cover said camera head and camera cable while said second bag covers said light guide cable and said sterilized endoscope is substantially uncovered by either of said component bags;
   c) means engaged to said first end of said first component bag for sealably attaching said bag to the endoscope in the region of attachment of said light guide cable to said endoscope;
   d) means for sealably securing the second ends of said first and second bags to said light guide cable and to said camera cable at predetermined distances from a working area; and
   e) the exposed outer surfaces of said first and second component bags are sterile.

2. Apparatus as defined in claim 1 further including:

a) an endoscope hub located at the proximal end of said endoscope adapted to receive said camera head and said light guide cable; and b) said hub is substantially positioned within said first bag.

3. Apparatus as defined in claim 2 further characterized in that said first and said second component bag each comprises an extendible folded configuration.

4. Apparatus as defined in claim 3 further comprising a heat sealed seam for engaging said first bag to said second bag.

5. Apparatus as defined in claim 4 wherein each of said component bags includes at least one tab adjacent its free end.

6. Apparatus as defined in claim 5 wherein each of said component bags is of plastic.

7. Apparatus as defined in claim 6 wherein each of said component bags is formed of polyethylene.

8. Apparatus as defined in claim 7 wherein said component bags are less than 3 mils thickness.

9. Apparatus for use with an endoscopic system of the type that includes an endoscope having a rigid probe, an optical adapter attached between the proximal end of said endoscope and a camera head, a light guide cable, and a camera cable for transmitting power and data between said camera head and a source comprising, in combination:

a) a first elongated component bag having opposed open ends and having a transversely-oriented aperture adjacent a first end thereof;

b) a second elongated component bag having opposed open ends, a first end of said bag being sealably secured to said first bag at said aperture so that the interior of said first component bag communicates with the interior of said second component bag through said aperture;

c) an elongated rigid cylindrical shield having oppositely-disposed proximal and distal ends, the length of said shield exceeding that of said rigid probe and the inner diameter thereof exceeding the outer diameter of said probe;

d) means for attaching the proximal end of said shield to said first end of said first bag;

e) means for sealably securing said second ends of said first and second component bags to said optical cable and to said camera cable at predetermined distances from an instrument working area; and f) the outer surfaces of said shield, said first and said second component bags are sterile.

10. Apparatus as defined in claim 9 further characterized in that each of said first and second component bags comprises an extendible folded configuration.

11. Apparatus as defined in claim 10 wherein said cylindrical shield further includes:

a) an optically clear window; and b) said window is fixed to the distal end of said shield.

12. Apparatus as defined in claim 11 further comprising a heat sealed seam for engaging said first bag to said second bag.

13. Apparatus as defined in claim 12 wherein each of said component bags includes at least one tab adjacent its free end.

14. Apparatus as defined in claim 13 wherein each of said component bags is of elastomeric material.

15. Apparatus as defined in claim 14 wherein each of said component bags is formed of polyethylene.

16. Apparatus as defined in claim 11 wherein said window includes an anti-reflection coating.

17. Apparatus as defined claim 9 wherein said shield is plastic.

18. Apparatus as defined in claim 9 wherein said shield is metallic.

* * * * *